US006508784B1

(12) United States Patent
Shu (10) Patent No.: US 6,508,784 B1
(45) Date of Patent: Jan. 21, 2003

(54) BALLOON CATHETER HAVING ADJUSTABLE CENTERING CAPABILITIES AND METHODS THEREOF

(76) Inventor: Yan-Ho Shu, 7358 Trade St., San Diego, CA (US) 92121

( * ) Notice: Subject to any disclaimer, the term of this patent is extended or adjusted under 35 U.S.C. 154(b) by 0 days.

(21) Appl. No.: 09/575,869

(22) Filed: May 19, 2000

(51) Int. Cl.[7] ............................................. A61M 29/00
(52) U.S. Cl. .................. 604/96.01; 604/508; 604/509; 604/20; 604/22; 600/3
(58) Field of Search ........................ 604/96.01, 104, 604/101.01, 264, 500, 508, 509, 20, 22; 600/3; 606/159, 198

(56) References Cited

U.S. PATENT DOCUMENTS

| 4,793,359 A | 12/1988 | Sharrow ..................... 128/658 |
| 5,087,247 A | 2/1992 | Horn et al. ..................... 604/98 |
| 5,122,125 A | 6/1992 | Deuss ......................... 604/282 |
| 5,179,961 A | 1/1993 | Littleford ..................... 128/772 |
| 5,199,939 A | 4/1993 | Dake et al. .................... 600/3 |
| 5,295,959 A | 3/1994 | Gurbel et al. .................. 604/96 |
| 5,295,960 A | 3/1994 | Aliahmad et al. ............. 604/96 |
| 5,295,995 A | 3/1994 | Kleiman ...................... 606/194 |
| 5,411,466 A | 5/1995 | Hess ............................ 600/3 |
| 5,522,961 A | 6/1996 | Leonhardt ................... 156/252 |
| 5,540,659 A | * 7/1996 | Tierstein ..................... 604/104 |
| 5,643,171 A | 7/1997 | Bradshaw et al. ............. 600/3 |
| 5,797,948 A | 8/1998 | Dunham ..................... 606/194 |
| 5,855,546 A | 1/1999 | Hastings et al. ............... 600/3 |
| 5,863,284 A | 1/1999 | Klein ............................ 600/3 |
| 5,882,291 A | 3/1999 | Bradshaw et al. ............. 600/3 |
| 5,891,091 A | * 4/1999 | Tierstein ..................... 604/104 |
| 5,899,882 A | 5/1999 | Waksman et al. ............. 604/96 |
| 5,910,101 A | 6/1999 | Andrews et al. ............... 600/3 |
| 5,910,102 A | 6/1999 | Hastings ....................... 600/3 |
| 5,938,582 A | 8/1999 | Ciamacco, Jr. et al. ......... 600/3 |
| 5,947,889 A | 9/1999 | Hehrlein ........................ 600/3 |
| 5,947,924 A | 9/1999 | Liprie .......................... 604/96 |
| 5,971,909 A | 10/1999 | Bradshaw et al. ............. 600/3 |
| 5,976,106 A | 11/1999 | Verin et al. ..................... 604/96 |
| 6,013,019 A | 1/2000 | Fischell et al. ................ 600/3 |
| 6,033,357 A | 3/2000 | Ciezki et al. .................. 600/3 |
| 6,033,398 A | * 3/2000 | Farley et al. .................. 604/20 |
| 6,045,495 A | 4/2000 | Weinberger .................... 600/3 |
| 6,048,299 A | * 4/2000 | Hoffmann ....................... 600/3 |
| 6,059,752 A | * 5/2000 | Segal .......................... 604/104 |
| 6,074,374 A | * 6/2000 | Fulton ...................... 604/96.01 |
| 6,179,788 B1 | * 1/2001 | Sullivan ................... 604/96.01 |
| 6,196,996 B1 | * 3/2001 | Tierstein ..................... 604/104 |
| 6,224,584 B1 | * 5/2001 | March et al. ................ 604/508 |
| 6,319,242 B1 | * 11/2001 | Patterson et al. ........... 604/508 |

OTHER PUBLICATIONS

"Radiopaque™ Ink: the high–tech alternative to platinum bands" product brochure, CI Incorporated.

* cited by examiner

Primary Examiner—Teresa Walberg
Assistant Examiner—Fadi H. Dahbour (57) ABSTRACT

A radiation treatment system comprising a balloon catheter and a treatment apparatus. A method for delivering radioactive dose adequately to treat eccentric atheroma comprises positioning a radiation source on the treatment apparatus to the eccentric atheroma for a predetermined treatment period, wherein the positioning of the radiation source over a balloon catheter is radially and/or axially adjustable. The balloon catheter has adjustable centering capability and comprises a tubular centering structure disposed at the distal end of the balloon catheter, wherein the centering structure comprises a plurality of balloon members that are independently radially expandable and adjustable in inflation size. The treatment apparatus is slidably positioned inside the lumen of the balloon catheter, wherein the treatment apparatus comprises a radiation source.

15 Claims, 7 Drawing Sheets

BALLOON CATHETER HAVING ADJUSTABLE CENTERING CAPABILITIES AND METHODS THEREOF

FIELD OF THE INVENTION

The present invention generally relates to improved medical devices and methods for use. More particularly, the present invention relates to a balloon catheter having adjustable capability for positioning and orienting the tip section resulting in more effective radioactive treatment of eccentric atheroma in a patient for use in association with coronary, renal, cerebral, and peripheral angioplasty/stenting.

BACKGROUND OF THE INVENTION

The primary methods of intervention for coronary artery diseases are coronary artery bypass graft surgery (CABG) and percutaneous transluminal coronary angioplasty (PTCA). In PTCA, a catheter equipped with an inflatable balloon is threaded intravascularly to the site of atherosclerotic narrowing of the vessel. Inflation of the balloon with concomitant compression of atheroma enlarges the atherosclerotic narrowing and enlarges the lumen by stretching the vessel wall. PTCA has emerged as a very effective alternative to CABG. That is, it is less invasive, has lower patient risks, and costs less than CABG.

The principle limitation of angioplasty is restenosis, a re-narrowing of the treated vessel to less than 50% of its original size. Studies have shown that restenosis affects 25–45% of PTCA patients, requiring re-intervention at some point in the first six months post the initial procedure. Stents have proven highly effective at reducing both elastic recoil of the arterial wall and vascular remodeling by holding the vessel open. Restenosis rates after stenting have been reported in the 20–30% ranges due to primarily intimal hyperplasia. Intimal hyperplasia is a physiological response to injury, similar to the scarring that occurs in wound healing. During the first few weeks after angioplasty, cells multiply on the inside of the artery, causing the inner lumen to shrink. Several approaches have been suggested and tried to reduce the restenosis rate with mixed results, including atherectomy, laser, cryo-ablation, thermo-ablation, ultrasound, calcium antagonists, fish oils, steroids, or the like.

Radiation seems to be effective at preventing smooth muscle cell proliferation by breaking the strands of DNA in living cells. One of the current radiation therapies is first to advance a flexible delivery balloon catheter through an artery or a vein of a patient until the distal tip is at or near the lesion region of the treated vessel. Subsequently, a treatment apparatus, comprising a wire or a small catheter having a radiation source at the tip is advanced through the delivery balloon catheter until the radiation source is disposed at the lesion region. The radiation source is held at the lesion region for a predetermined treatment period calculated to deliver an effective radioactive dose of radiation. Thereafter the treatment apparatus and the delivery balloon catheter are then withdrawn.

Hess in U.S. Pat. No. 5,411,466 teaches a method and apparatus for treating restenosis by positioning a radioactive dose to the region after angioplasty to inhibit restenosis. The catheter has at its distal end a radioactive source, wherein the source is maneurable to the site of a lesion allowing the site to be exposed to the radiation dose that will affect smooth muscle cells such that the rapid growth of such cells can be prevented, thereby controlling restenosis. This patent, however, does not address non-uniform irradiation, nor does it teach means for positioning and centering the radiation dose for effective irradiation on an essentially eccentric atheroma lesion region.

Treatment apparatus, such as a catheter or a wire has been disclosed. For example, U.S. Pat. No. 5,199,939 to Dake et al. discloses a radioactive catheter having a plurality of cylindrically shaped, radioactive pellets longitudinally spaced apart inside the lumen of the catheter. However, non-centering wire-carried radiation sources are sub-optimal in performance which has been disclosed by Dake et al. in U.S. Pat. No. 5,199,939 and Bradshaw in U.S. Pat. No. 5,643,171. Therefore, it would be highly desirable to provide a radiation delivery system that would assure that the source is somehow centered in the vessel for an essentially uniform atheroma lesion type or adjustably positioned about the center of the vessel for an eccentric atheroma lesion type.

Current balloon dilatation catheters employ a fixed or movable steerable guidewire which negotiates the serpentine coronary vasculature in an atraumatic fashion to provide a path for the passage of the balloon catheter. Apparatus for positioning a catheter distal tip is known and well practiced. U.S. Pat. No. 4,793,359 to Sharrow discloses a balloon near the tip of an angioplasty catheter for accurately establishing the position and orientation of the distal tip within an artery in response to the balloon dilation. The balloon comprises a distal wall portion substantially perpendicular to the central axis so as the catheter tip is placed in centered, coaxial relation to the balloon when the balloon is inflated. However, the atherosclerosis plaque is generally asymmetrically distributed around the artery wall. In an atherosclerotic artery, the balloon catheter as disclosed by Sharrow does not have an adjustable means for effectively positioning the distal tip.

U.S. Pat. No. 5,122,125 to Deuss discloses an angioplasty catheter having at least three radially protruding elements constructed of very soft material at its end portion so that a very great stability of the end portion is achieved against the surrounding vessel wall. However, the catheter still suffers the capability for adjusting its tip position and orientation for more effective irradiation therapy.

U.S. Pat. No. 5,179,961 to Littleford discloses a separate flexible tube having a peripherally expandable zone at the distal end of the tube so as to center and stabilize the flexible tube in place. A treatment catheter is then passed through the lumen of the flexible tube for tissue treatment. However, Littleford does not disclose a delivery catheter having an adjustable means for independently adjusting each of the expandable elements for effective positioning of the distal tip.

Aliahmad et al. in U.S. Pat. No. 5,295,960 discloses a catheter with balloon material or a membrane disposed interiorly of the catheter body in the inflation lumen so that the balloon material can be inflated to form at least one exterior balloon through holes of the catheter body at the end or the side of the catheter body. As disclosed, separate balloons formed from a single membrane can be deployed through respective openings circumferentially spaced or axially spaced. However, the balloon material or membrane does not have an adjustable means for independently adjusting each of the expandable balloons. The balloon material is not an integral part of the distal catheter body and may separate from the catheter body unexpectedly.

Inflation of conventional dilatation balloons completely blocks the artery, and thus interrupts distal coronary blood flow. Typical inflation time for radioactive treatment may range from 3 minutes to 60 minutes. Maintenance of coronary perfusion during dilation would greatly enhance the safety of coronary angioplasty, particularly in vessels serving large areas of myocardium. Therefore, it would be desirable for a radioactive treatment apparatus or delivery balloon catheter to provide for continuous blood flow (perfusion) past the stenotic region in the target coronary vessel.

U.S. Pat. No. 5,087,247 to Horn et al. and No. 5,295,995 to Kleiman disclose perfusion dilatation catheter having some clearance between the inflated balloon and the vessel wall so that continuous perfusion is maintained. Particularly, U.S. Pat. No. 5,295,995 shows an inflatable non-circular balloon, wherein the balloon tip has at least two substantially rounded axial protrusions or apices which, upon expansion of the balloon, come into apposition with the walls of the target vessel and form blood flow paths around the protrusions. The inflated balloon does not have adjustable means for effective positioning of the catheter tip for subsequent radiation treatment.

Numerous balloon catheters which afford varying degrees of coronary perfusion during balloon radioactive treatment have been described in the prior art. However, none of these catheters incorporate all of the necessary attributes mentioned above into a single device with adjustable centering capability at its distal tip portion.

Although a variety of procedures have been proposed for irradiating a treated vessel region, most of such procedures lack the ability to conveniently and effectively introduce a radiation source uniformly within the lesion vessel region preferably over a short treatment period. The "uniformity of radiation source within the lesion vessel region" is referred to and defined in this invention as the appropriately proportional exposure of the radiation according to the need of the atheroma for radiation. In other words, more radiation shall be directed to the lesion region that needs more therapeutic dose.

Since majority of the atherosclerosis or the compressed atheroma is eccentric around the vessel wall, a radiation source should be adjusted to provide proportionally effective radiation dose according to the need of the site-specific atheroma for radiation treatment. This may also apply to the bifurcation or tortuous branch vessels. The radiation dose should be adjusted axially, radially, or a combination of axial and radial adjustment on a need basis for optimal tissue treatment.

Therefore, it would be desirable to provide methods and apparatus that would reduce or greatly eliminate such drawbacks of inefficient radiation so as to allow for the introduction and withdrawal of the radioactive source and provide for the proportionally effective dose to the lesion vessel region without suffering the above-discussed disadvantages.

SUMMARY OF THE INVENTION

In general, it is an object of the present invention to provide a device and methods for delivering radioactive dose adequately to treat essentially eccentric atheroma comprising positioning a radiation source close to the eccentric atheroma for a predetermined treatment period, wherein the positioning of the radiation source is adjustable. The modes for making the radiation source adjustable may include manual adjustment, auto-adjustment, continuous adjustment, rotatable adjustment, back-and-forth adjustment, programmed adjustment, and the like. Furthermore, the modes for making the radiation source adjustable may include a movable or rotatable radiation source during the radiation procedures.

The device may comprise a balloon catheter having adjustably centering capability and a treatment apparatus to be inserted within the catheter having radiation source for treating eccentric atheroma. It is another object of the present invention to provide a device and methods for positioning a radiation source axially adjustable, radially adjustable, combination of axially and radially adjustable, and the like with respect to the eccentric atheroma in a blood vessel. The adjustable centering process may be performed to a lesion region once or adjusted more than once for effective radiation therapy. It is still another object of the present invention to provide a device and methods for positioning a radiation source comprising a plurality of balloons disposed at a distal section of the device, wherein the plurality of balloons may be independently adjustable in inflation size, shape, diameter to stabilize the distal section of the device, such as a balloon catheter, with respect to the lesion region requiring radiation treatment.

In accordance with one embodiment of the invention, the eccentric atheroma is restenosis, preferably resulting from angioplasty, atherectomy, laser angioplasty, stenting, combination of angioplasty and stenting, or the like. Since atherosclerosis or arteriosclerosis is seldom uniformly distributed within the vessel wall, the eccentric atheroma in this invention includes essentially all types of atherosclerosis/arteriosclerosis before and/or after a procedure, such as angioplasty, stenting, atherectomy, surgery or the like.

In some cases, it may be desirable to maintain the radiation sources at a treatment region for an extended treatment period. For instance, in some cases it may be desirable to maintain the radioactive sources at a treatment site for up to about 20 minutes or more. It is one object of the present invention to provide perfusion schemes so that adequate blood flow is provided for flowing between any two of the balloon members.

In another preferred embodiment of the present invention, a radiation treatment system comprises a balloon catheter having adjustable centering capability, the balloon catheter comprising an elongated catheter shaft having a shaft distal end, a shaft proximal end, a shaft distal section, and a plurality of lumens between the shaft distal end and the shaft proximal end. A tubular centering structure is disposed at the shaft distal end, wherein the tubular centering structure comprises a plurality of balloon members that are radially expandable or inflatable, wherein each of said plurality of balloon members is independently adjustable in inflation size, shape, or diameter. Each of said plurality of balloon members is connected to and communicated to one of the plurality of lumens for balloon inflation using inflation fluid and deflation thereafter. The radiation treatment system further comprises a treatment apparatus slidably positioned inside one of the lumens, wherein the treatment apparatus comprises a radiation source.

In still another preferred embodiment, the tubular centering structure of the balloon catheter has an outer diameter essentially equivalent to an outer diameter of the catheter shaft. One of the lumens of the balloon catheter may be a lumen for passing or riding on a guide wire. The tubular centering structure of the balloon catheter may be made of material selected from elastomers consisting of polyurethane, silicone, blend of polyurethane and silicone, natural rubber, synthetic rubber, polyisoprene, polyisobutylene, nylon block copolymer, latex, polyethylene, copolyester, fluorocopolymer, SBR, and the like. The elongated catheter shaft of the balloon catheter may be made of material selected from the group consisting of polyethylene, polyimide, polypropylene, nylon, polyvinyl chloride, their mixture, and the like. The above-referred material is biocompatible and has been widely used for balloon and catheter body construction. Optionally, at least two of the balloon members of the tubular centering structure are positioned at different locations axially from one another.

The tubular centering structure or the shaft distal section of the balloon catheter may be imprinted with radiopaque ink for tracking exact location of the balloon catheter inside a patient. In another preferred embodiment, at least one radiopaque marker may be disposed at the shaft distal section or the distal element of the balloon catheter for tracking exact location of the balloon catheter inside a patient, wherein the distal element of the balloon catheter may be disposed distal to the tubular centering structure. In another preferred embodiment, the distal element has a lumen for inserting a guidewire.

In accordance with another embodiment of the invention, there is provided a method for treating restenosis of a lesion region of a patient comprising the steps of (a) inserting a balloon catheter through a body conduit to said lesion region of the patient, wherein the balloon catheter comprises a tubular centering structure disposed at a distal section of the balloon catheter, wherein the tubular centering structure comprises a plurality of balloon members that are independently radially expandable; (b) inflating each of the balloon members independently and adjustably in desired inflation size to stabilize the distal section of the balloon catheter with respect to the lesion region; (c) inserting a treatment apparatus inside a lumen of the balloon catheter, wherein the treatment apparatus comprises a radiation source; (d) positioning the radiation source at about the lesion region; (e) holding the radiation source for a predetermined treatment period for treating restenosis; and (f) withdrawing the treatment apparatus.

To place the radiation sources in apposition with the vessel wall in a desired pattern, the invention employs a radially expandable tubular centering structure having a plurality of individually adjustable balloon members. The adjustable balloon member is radially expandable. Exemplary radially expandable balloon members of the tubular centering structure may comprise semi-compliant balloon and compliant balloon, such as a conventional angioplasty balloon, elastomeric balloons, and the like. The elastomeric balloon may preferably be constructed of materials selected from the group consisting of polyurethane, silicone, blend of polyurethane and silicone, natural rubber, synthetic rubber, polyisoprene, polyisobutylene, nylon block copolymer, latex, polyethylene, copolyester, fluorocopolymer, SBR, and the like. The semi-compliant balloon may preferably be constructed of materials selected from the group consisting of polyethylene, nylon or the like.

The radiation sources may preferably emit gamma ($\gamma$) radiation, beta ($\beta$) radiation, or combination of gamma and beta radiation. Exemplary of radiation sources include $^{90}$Strontium, $^{90}$Yttrium, $^{125}$Iodine, $^{192}$Iridium and the like. The radiation sources may preferably comprise a plurality of discrete elements, such as seeds, elongate strips, ribbons, wires, ribs and the like. The effective dose to inhibit smooth muscle cell hyperplasia and the resulting restenosis is approximately a few thousand rads, preferably 1,000 to 5,000 rads. For a given source, the intensity of the radiation drops rapidly as a function of the distance from the source. Accordingly, if the source is not held reasonably near the lesion region, for a given treatment period, the portion of the vessel wall may not receive adequate dose of radiation, while the portion of the non-lesion region may receive more than prescribed dose. Overdosing of a section of blood vessel may cause arterial necrosis, inflammation and hemorrhage. Underdosing may result in no inhibition of smooth muscle cell proliferation or even exacerbation of the hyperplasia and resulting restenosis.

In one preferred embodiment, a method of delivering radiation dose comprises disposing the radiation source at a tip portion of a treatment apparatus, wherein the treatment apparatus is a wire, a catheter, a combination of wire and catheter, and the like. The tip portion of the treatment apparatus may optionally be adjustable, wherein the modes for making the radiation source adjustable may include manual adjustment, auto-adjustment, continuous adjustment, rotatable adjustment, back-and-forth adjustment, programmed adjustment, and the like.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

With reference to the drawings FIGS. 1 to 7, what is shown is an embodiment of a radiation treatment system comprising a balloon catheter having adjustable centering capability and a treatment apparatus to be inserted within the balloon catheter having radiation source for treating eccentric atheroma or various types of restenosis.

Figure 1:
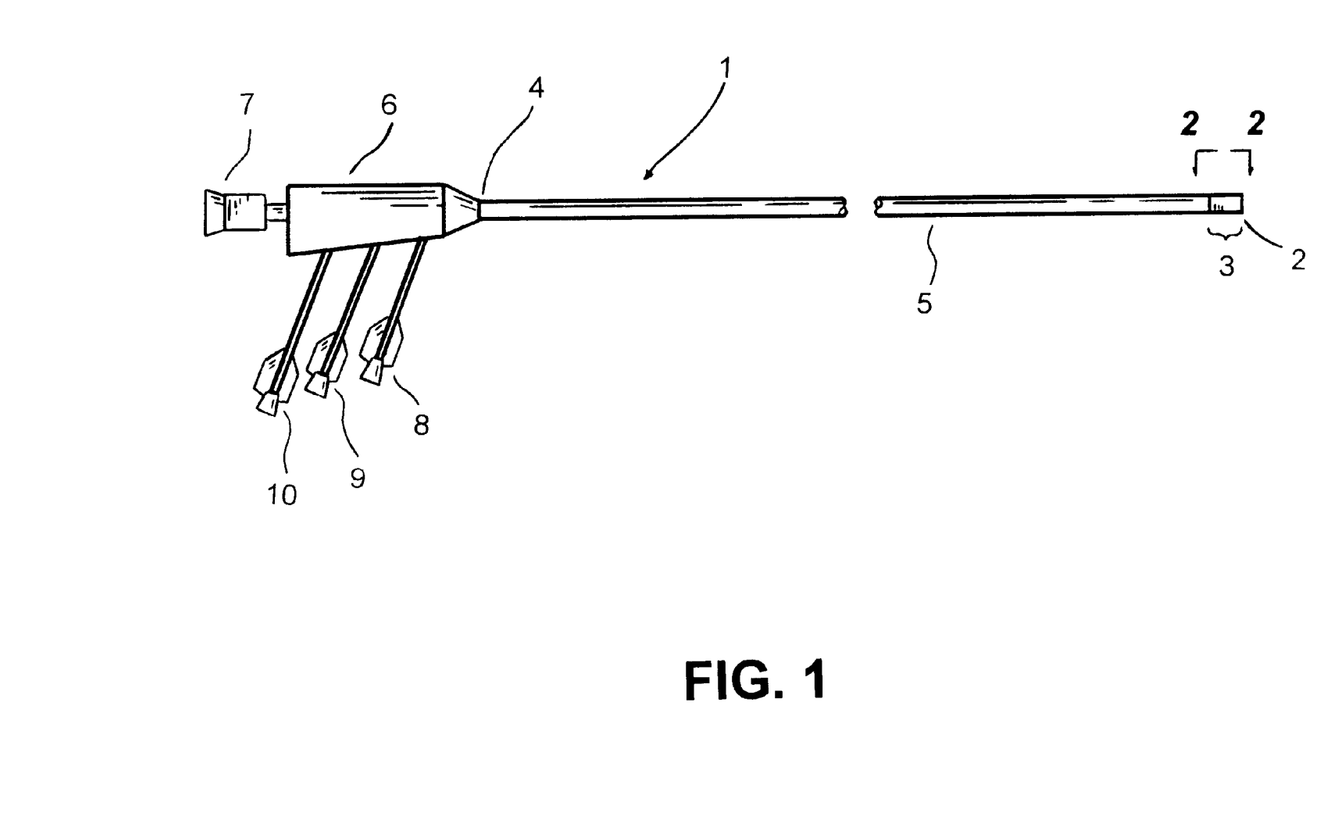
FIG. 1 is an overall view of a radiation treatment system comprising a balloon catheter with adjustable centering capability and a treatment apparatus with a radiation source according to the principles of the present invention.

FIG. 1 shows an overall view of a radiation treatment system comprising a balloon catheter with adjustable centering capability and a treatment apparatus with a radiation source according to the principles of the present invention. A balloon catheter 1 comprises an elongated catheter shaft 5 having a shaft distal end 2, a shaft proximal end 4, a shaft distal section, and a plurality of lumens between the shaft distal end 2 and the shaft proximal end 4. A handpiece, adapter, or connector type luer 6 is secured to the proximal end 4. The handpiece 6 is equipped with a plurality of inflation means 8, 9, 10 for providing inflation fluid to inflate each of the inflatable balloons and deflate thereafter. Each inflation means is independently connected to one balloon member through a lumen.

Figure 2:
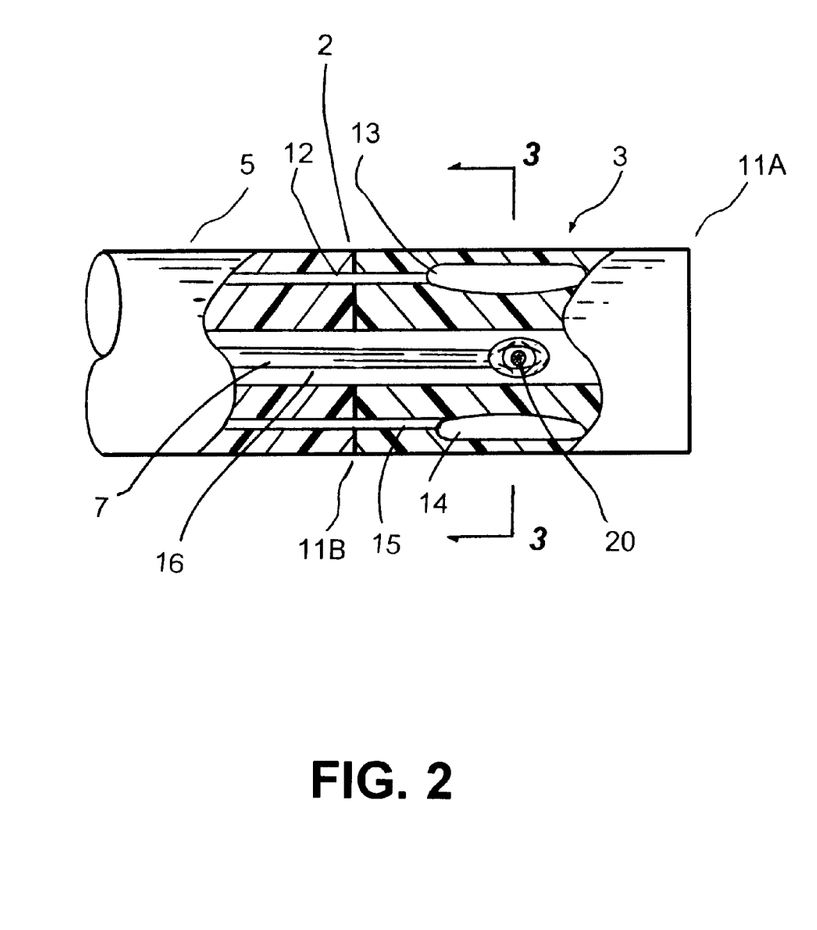
FIG. 2 is a close-up axial cross-sectional view of section 2—2 of FIG. 1 having a plurality of balloon members with adjustable centering capability.

FIG. 2 shows a close-up axial cross-sectional view of section 2—2 of FIG. 1 having a plurality of balloon members with adjustable centering capability. A tubular centering structure 3 is disposed at the shaft distal 2, wherein the tubular centering structure 3 comprises a distal end 11A, a proximal end 11B, and a plurality of balloon members 13, 14 that are radially expandable or inflatable, wherein each of the plurality of balloon members 13, 14 is independently adjustable in inflation size, shape or diameter. One balloon member 13 is connected to and communicated to one lumen 12 of the plurality of lumens for balloon inflation and deflation, while the other balloon member 14 is connected to another lumen 15 for balloon inflation and deflation. In a preferred embodiment, at least two balloon members of the tubular centering structure may be positioned at different locations axially from one another.

A treatment apparatus 7 is slidably positioned inside one lumen 16 of said plurality of lumens of the balloon catheter 1, wherein the treatment apparatus comprises a radiation source 20. The treatment apparatus may be a wire, a small catheter, or the like that has a retaining means for holding the radiation source 20 at the distal end of the treatment apparatus 7. In another preferred embodiment, the distal end of the treatment apparatus 7 is adjustable by a clinician for effective positioning of the radiation source 20 with respect to the eccentric atheroma in radiation treatment.

The material associated with the balloon members may typically be more flexible than the material associated with the catheter shaft. The durometer of the material forming the catheter shaft may preferably be in a range from Shore 5A to Shore 100D. A range of particular advantage occurs from a Shore hardness of 35D to 100D for strength and pushability. In comparison, the material forming the balloon members may preferably have a durometer between Shore 5A and Shore 80D. A preferred range of durometer might be between Shore 25A and Shore 100A. The thermoplastic and thermoset materials which are of particular interest for the catheter shaft include rubbers, elastomers, silicone, polyimide, polyvinyl chloride, polyethylene, polypropylene, nylon, polycarbonates, and their mixture. Material of interest for the tubular centering structure includes polyurethane, silicone, blend of polyurethane and silicone, natural rubber, synthetic rubber, polyisoprene, polyisobutylene, nylon block copolymer, latex, polyethylene, copolyester, fluorocopolymer, SBR, and the like their mixture/copolymer.

Figure 3:
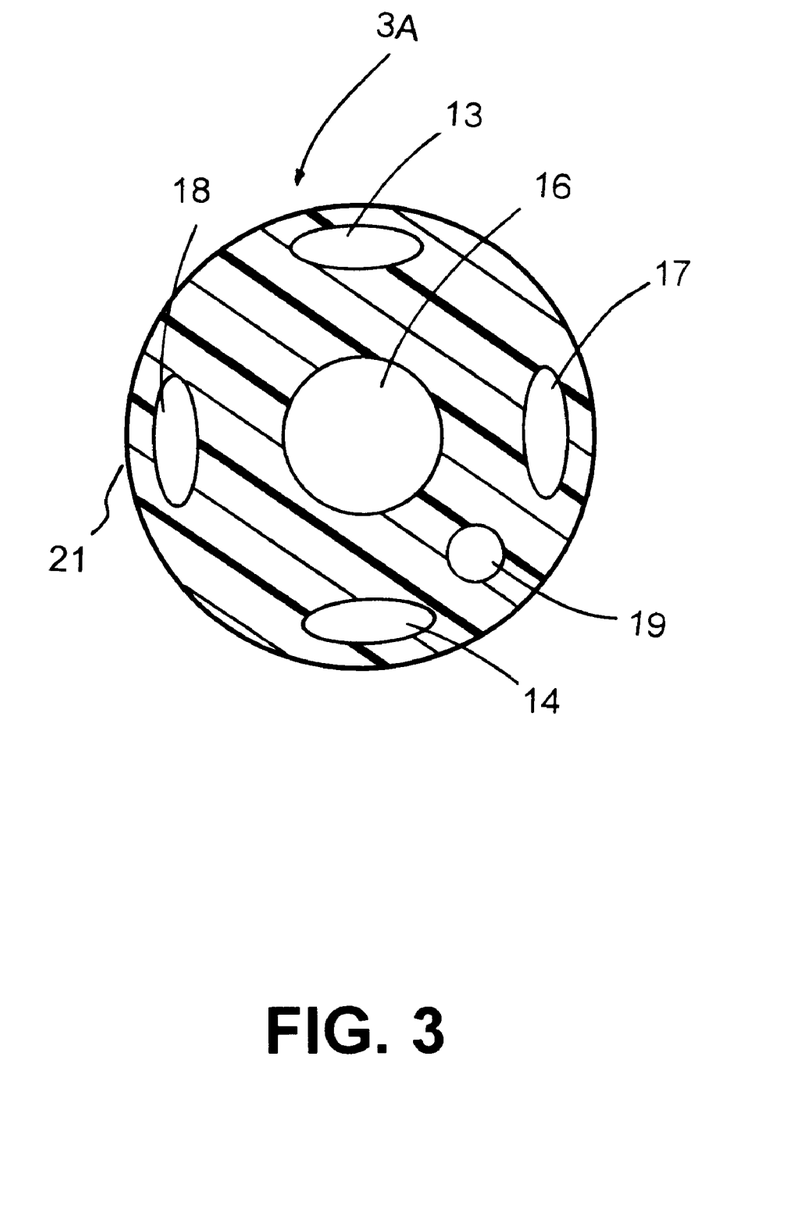
FIG. 3 is a transverse cross-sectional view of section 3—3 of FIG. 2 having a plurality of balloon members with adjustable centering capability at a non-inflated state.

FIG. 3 shows a transverse cross-sectional view of section 3—3 of FIG. 2 for the tubular centering structure 3A having a plurality of balloon members 13, 14, 17, 18 with adjustable centering capability at a non-inflated state. Each balloon member is connected to its own inflation means for providing inflation fluid and may be inflated independently in a radially outwardly manner. The balloon material surrounding each balloon member may be constructed from the same material as the tubular centering structure 3A. In a preferred embodiment, the balloon material between one of the balloon members 13, 14, 17, 18 and the outer peripheral 21 may be constructed from an inflatable material that is different from the bulk of the tubular centering structure 3A. A lumen 19 may be employed for passing a guide wire. The lumen 16 is used for loading the treatment apparatus having a radiation source. In a further embodiment of the present invention, the balloon catheter may further comprise a distal element that is distal to the tubular centering structure, wherein the distal element comprises a lumen for guide wire insertion. The distal element may be a short tubing having about the same outer diameter as that of the balloon catheter.

The construction of the tubular centering structure having a plurality of balloon members may be achieved by one of several different methods, and any of the following methods may be used, alone or in combination. One method of manufacturing the tubular centering structure includes using heat and a mold, i.e. a glass mold, and shaping the balloon members portion so as to impart the desired configuration. The mold is usually coated with a mold-releasing lubricant to prevent adherence of the plastic to the mold. Then a thermoplastic polymer or other polymeric material is heated and shaped by expanding it under pressure to conform to the mold so as to form the desired configuration of the tubular centering structure with desired balloon members.

A second method of manufacturing the tubular centering structure is to use a multi-lumen tubing by sealing all but one lumens from one end. The unsealed lumen may be reserved for guide wire use. To make any luminal space as a balloon member, block a portion of the lumen longitudinally along the lumen so as to constrain the expansion of portions of the balloon perimeter during inflation. By constraining portions of the balloon perimeter during its expansion, one can achieve the desired configuration of the balloon members.

The proximal end of the tubular centering structure is joined to the distal end of the catheter shaft by orienting each lumen from both parts so that the lumen from the catheter shaft is connected to and in communication with the counterpart lumen of the tubular centering structure. Similarly, the proximal end of the distal element may be joined to the distal end of the tubular centering structure. The method of joining two plastic parts may include adhesive, solvent, melt, heat, or other appropriate means.

The tubular centering structure in its preferred embodiment may have an outside diameter ranging from about 2.0 to 4.0 millimeters with a wall thickness as thin as 0.01 millimeters. The balloon member will generally be from about approximately 1 cm to 5 cm in length. Such a balloon can be inflated to a few millimeters so as to stabilize the tubular centering structure preferentially close to the eccentric atheroma for later radiation treatment use. The tubular centering structure of the balloon catheter has an outer diameter essentially equivalent to an outer diameter of the catheter shaft or a little smaller.

Figure 4:
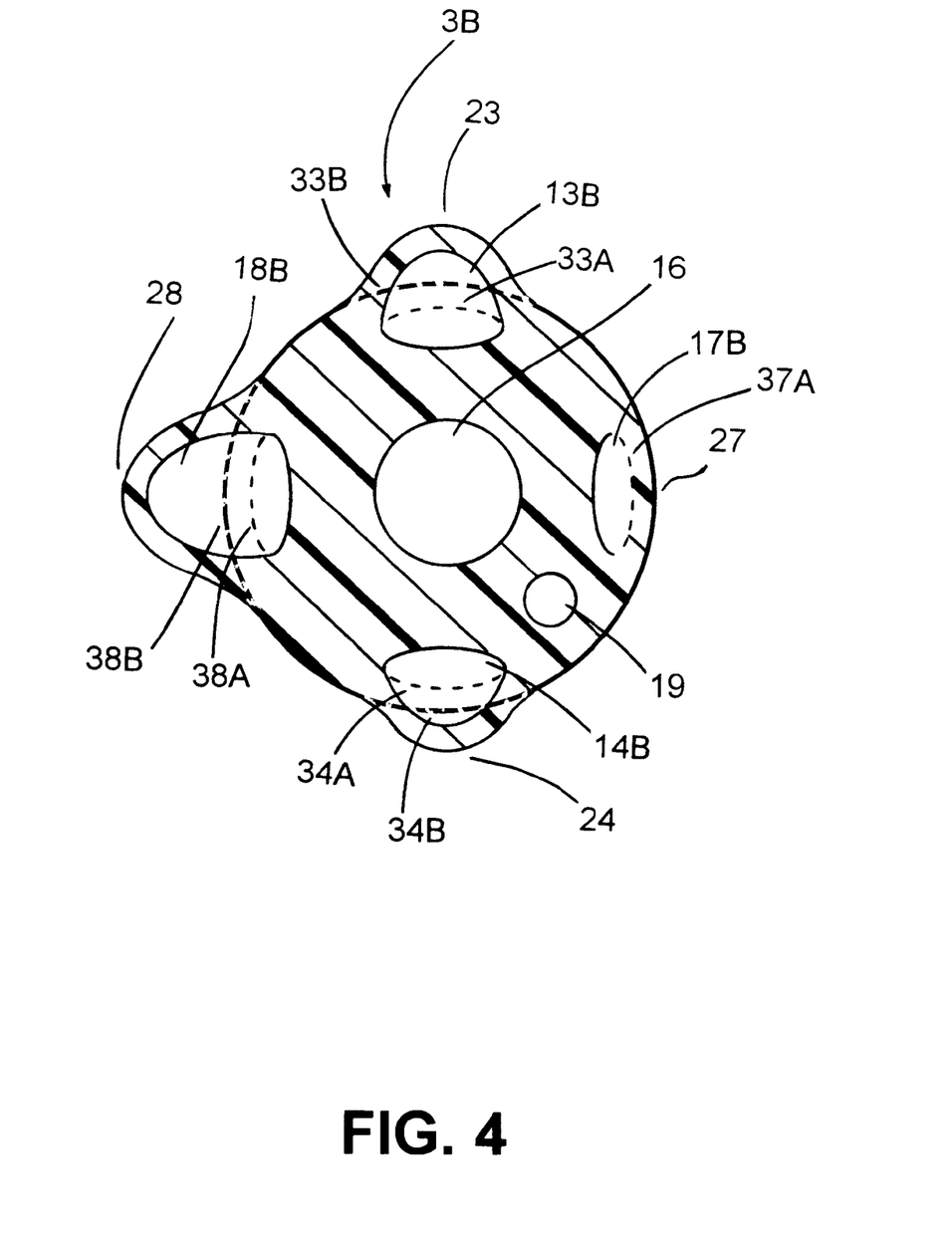
FIG. 4 is a transverse cross-sectional view of section 3—3 of FIG. 2 having a plurality of balloon members with adjustable centering capability at an inflated state.

FIG. 4 shows a transverse cross-sectional view of section 3—3 of FIG. 2 for the tubular centering structure 3B having a plurality of balloon members 13B, 14B, 17B, and 18B with adjustable centering capability at an inflated state. Each balloon member may be inflated independently, for example 13B, 14B, and 18B; or not inflated at all, for example 17B. The inflation is preferred in a radially outwardly manner. As shown in FIG. 3 and FIG. 4, the dotted lines 33A, 34A, 37A, 38A designate the pre-inflation boundary lines of the balloon members 13, 14, 17, and 18, respectively. The dotted lines 33B, 34B, 38B designate the pre-inflation peripheral line 21 of the tubular centering structure 3A. Each of the inflated lines 23, 24, 28 designates the line after their respective balloon member 13, 14, or 18 is independently expanded at various balloon inflation size, shape or diameter. One 19 of the plurality of lumens may be used for passing or riding on a guide wire while another 16 of the lumens is used for inserting a treatment apparatus within the balloon catheter. By inflating each balloon member at different inflation size, the mode of positioning the radiation source may be axially adjustable, radially adjustable, or the like with respect to the eccentric atheroma.

Figure 5:
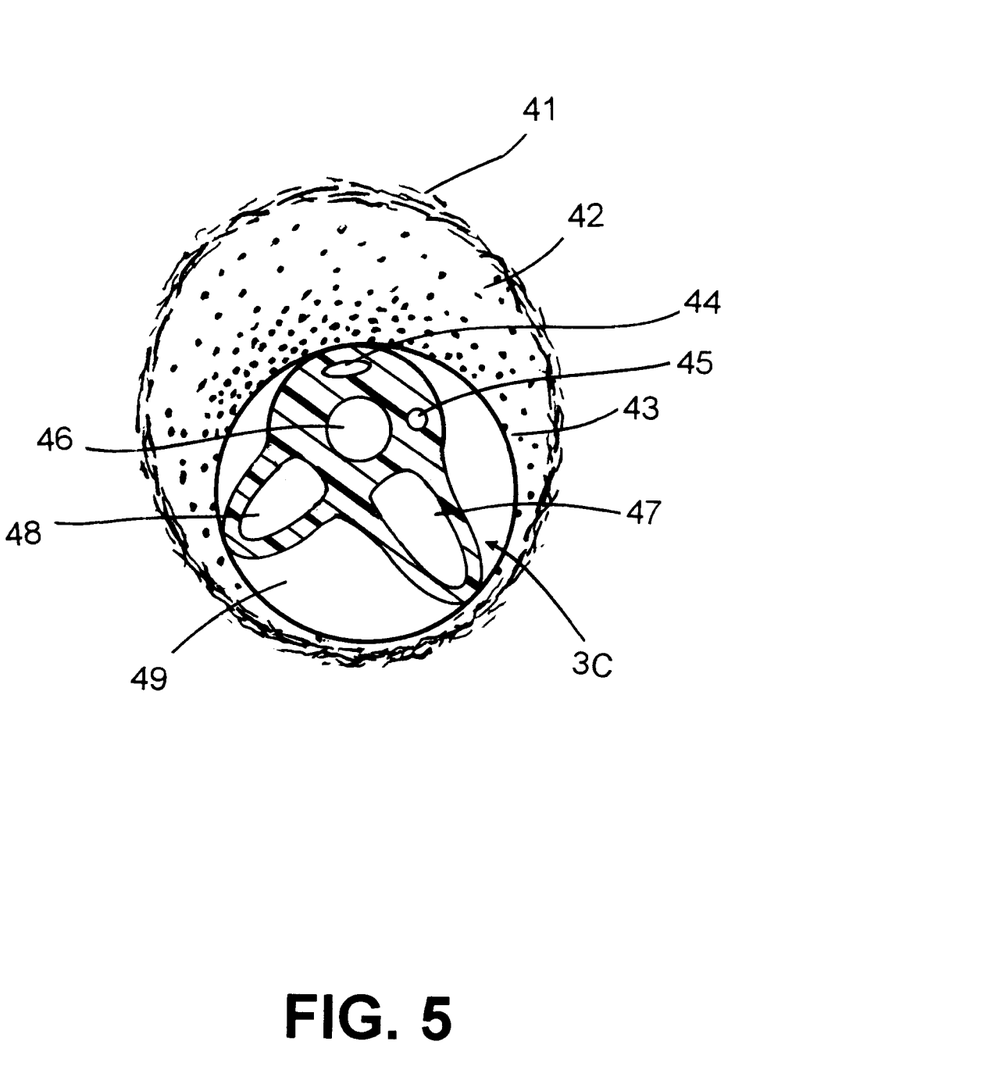
FIG. 5 is a simulated cross-sectional view of a tip section of the radiation balloon catheter at an inflated state, illustrating close proximity of the radiation source to a compressed atheroma.

FIG. 5 shows a simulated cross-sectional view of a tip section of the radiation balloon catheter at an inflated state, illustrating close proximity of the radiation source to the compressed atheroma or eccentric atheroma. After an angioplasty and/or stenting procedure, a stent 43 has been implanted to compress the atheroma 42 of a blood vessel 41 and enlarge the lumen 49. In a preferred embodiment as shown in FIG. 5, a catheter with three balloon members 44, 47, 48 is employed. To keep the treatment lumen 46 that is used for inserting a treatment apparatus having a radiation source close to the lesion region, a balloon 44 is optionally not inflated. The other two balloon members 47 and 48 are inflated so that to stabilize the distal section of the balloon catheter with respect to the lesion region. By adjusting and orienting the tubular centering structure 3C to proximity of the desired lesion region, optimal radiation treatment will be achieved when a radiation source is placed within the lumen 46. The lumen 45 may be used for passing or riding on a guide wire.

Figure 6:
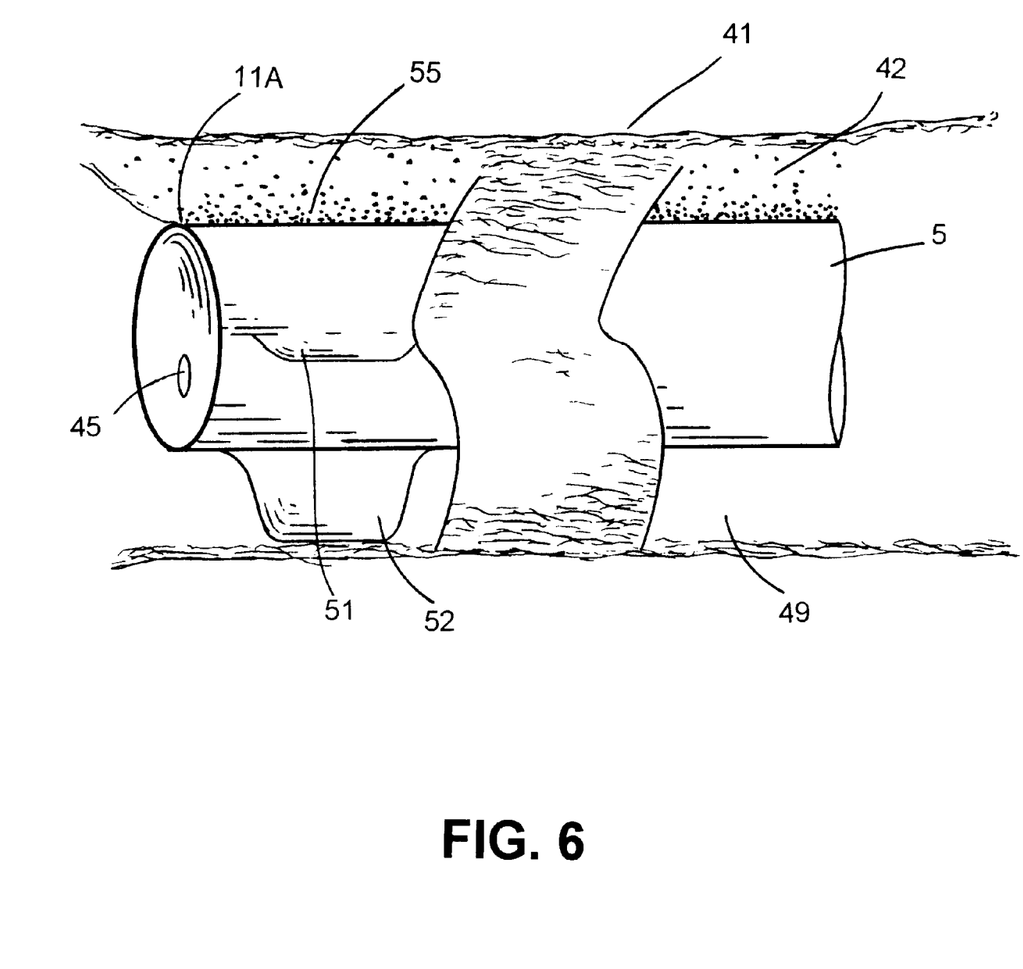
FIG. 6 is a perspective view of the tip section of the radiation balloon catheter simulating the adjustable centering of the balloon catheter at an inflated state.

FIG. 6 shows a perspective view of the tip section of the radiation balloon catheter at an inflated state. A balloon catheter 5 is inserted through the enlarged lumen 49 and positioned at about the lesion region 42. The distal section of the balloon catheter 5 is adjusted and oriented to proximity of the desired lesion region 55 by expanding the balloon members 51, 52 to substantially the opposite side of the lesion region 55.

Figure 7:
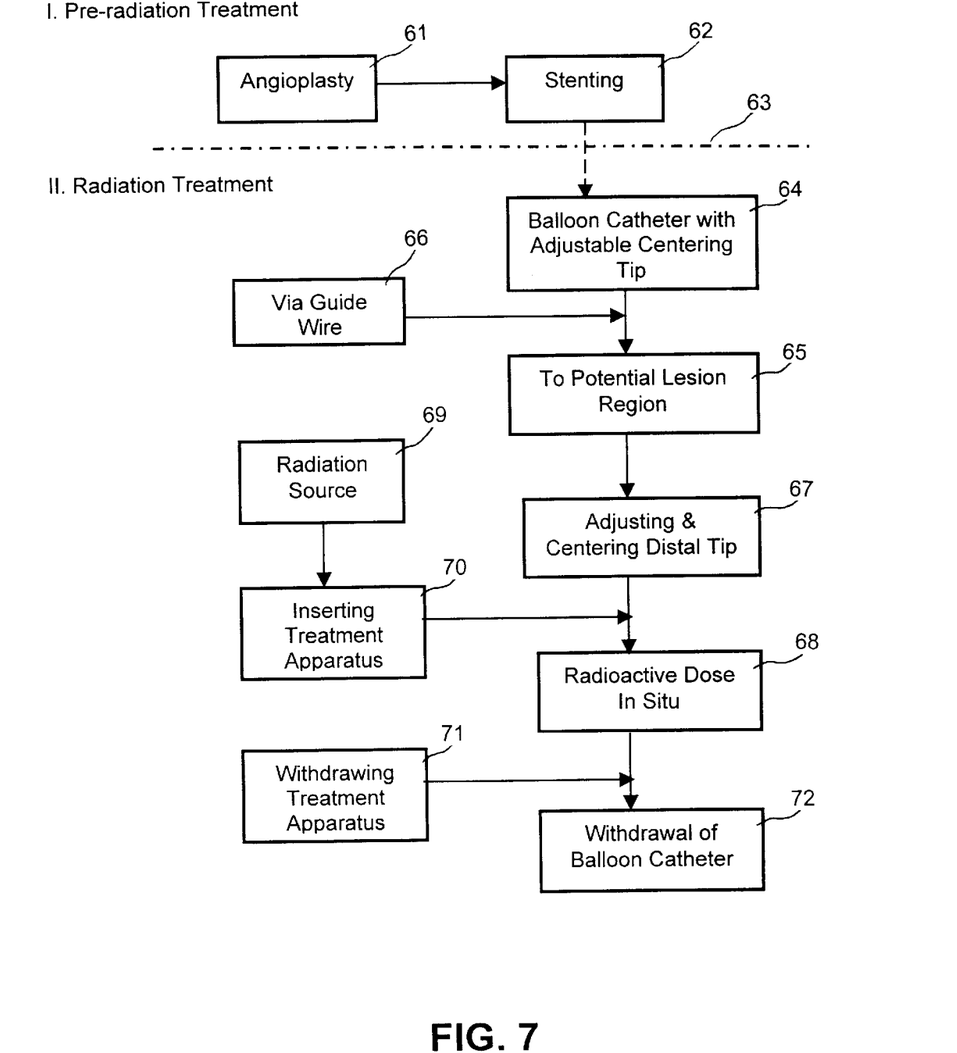
FIG. 7 is a schematic diagram illustrating one embodiment of the present invention for performing the radiation treatment method with a balloon catheter having adjustable centering capability.

FIG. 7 shows a schematic diagram illustrating one embodiment of the present invention for performing the radiation treatment method with a balloon catheter having adjustable centering capability. The phase I treatment illustrates a pre-radiation treatment, which may include angioplasty 61 and/or stenting 62. After the lumen is enlarged, Phase II radiation treatment 63 of the present invention may be initiated. A method for treating restenosis of a lesion region of a patient comprises the steps of inserting a balloon catheter 64 through a body conduit to the lesion region 65 of the patient. The insertion of a balloon catheter 64 may be assisted through a guide wire 66 disposed at about the distal portion of the balloon catheter 64. The balloon catheter 64 may comprise a tubular centering structure disposed at a distal section of the balloon catheter 64, wherein the centering structure comprises a plurality of balloon members that are radially expandable or inflatable. The method further comprises inflating each of the balloon members independently and adjustably in inflation size, shape or diameter to stabilize the distal section 67 of the balloon catheter with respect to the lesion region.

For radiation treatment process, inserting a treatment apparatus 70 inside a lumen of the balloon catheter 64, wherein the treatment apparatus comprises a radiation source 69. Then positioning the radiation source at about and close to the target lesion region and holding the radiation source for a predetermined treatment period for treating restenosis 68. After radiation treatment is done, withdrawing 71 the treatment apparatus and withdrawing 72 the balloon catheter.

To enhancing the tracking and location of the radiation treatment system inside the body, at least one radiopaque marker may be disposed at the shaft distal section or near the distal portion of the balloon catheter for tracking exact location of the balloon catheter inside a patient. In a preferred embodiment, platinum or gold may be employed for radiopaque viewing, imaging, and tracking. In another embodiment, the tubular centering structure of the balloon catheter may be imprinted with radiopaque ink for tracking exact location of the balloon catheter inside a patient. For example, the radiopaque ink from CI Incorporated (Norton, Mass.) may be used. The radiopaque ink is readily biocompatible and can be made to adhere to any surface which will not fall off or compromise the integrity of the medical device. By absorbing x-ray, radiopaque ink markers on the radiation treatment system of the present invention will be easily visible using fluoroscopy. The radiopaque ink can also be imprinted on the treatment apparatus for tracking.

From the foregoing description, it should now be appreciated that a radiation treatment system comprising a balloon catheter having adjustable centering capability and a treatment apparatus to be inserted within the balloon catheter having radiation source for treating eccentric atheroma or various types of restenosis has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A method for delivering radioactive dose adequately to treat eccentric atheroma comprising positioning a radiation source close to said eccentric atheroma for a predetermined treatment period, wherein said positioning of the radiation source is adjustable, and wherein said method of positioning said radiation source comprises a plurality of balloons disposed at a distal section of a balloon catheter, said plurality of balloons being independently adjustable in inflation size.

2. A radiation treatment system comprising:

a balloon catheter having adjustable centering capability, said balloon catheter comprising an elongated catheter shaft having a shaft distal end, a shaft proximal end, a shaft distal section, and a plurality of lumens between the shaft distal end and the shaft proximal end;

a tubular centering structure disposed at the shaft distal end, wherein said centering structure comprises a plurality of balloon members that are radially expandable, wherein each of said plurality of balloon members is independently adjustable in inflation size;

each of said plurality of balloon members being connected to and communicated to one of said plurality of lumens for balloon inflation and deflation; and a treatment apparatus slidably positioned inside one of said plurality of lumens of the balloon catheter, wherein said treatment apparatus comprises a radiation source.

3. A radiation treatment system according to claim 2, wherein said centering structure of the balloon catheter has an outer diameter essentially equivalent to an outer diameter of said catheter shaft and one of said plurality of lumens of the balloon catheter is a lumen for passing a guide wire.

4. A radiation treatment system according to claim 2 further comprising a distal element that is distal to said tubular centering structure, wherein said distal element comprises a lumen.

5. A radiation treatment system according to claim 2, wherein said centering structure of the balloon catheter is made of material selected from the group consisting of polyurethane, silicone, copolymer of polyurethane and silicone, natural rubber, synthetic rubber, elastomers, nylon, latex, polyethylene, polyethylene terephthalate, polyethylene terephthalate glycol, polyisoprene, polyisobutylene, and their mixture.

6. A radiation treatment system according to claim 2, wherein said elongated catheter shaft of the balloon catheter is made of material selected from the group consisting of polyethylene, polyimide, polypropylene, nylon, polyvinyl chloride, and their mixture.

7. A radiation treatment system according to claim 2, wherein said radiation source of the treatment apparatus is selected from the group consisting of beta radiation, gamma radiation, and combination of beta and gamma radiation.

8. A radiation treatment system according to claim 2, wherein at least two of said plurality of balloon members of said tubular centering structure are positioned at different locations axially from one another.

9. A radiation treatment system according to claim 2, wherein said centering structure of the balloon catheter is imprinted with radiopaque ink for tracking exact location of the balloon catheter inside a patient.

10. A radiation treatment system according to claim 2, wherein at least one radiopaque marker is disposed on the balloon catheter for tracking exact location of the balloon catheter inside a patient.

11. A radiation treatment system according to claim 2, wherein said balloon catheter further comprises a distal element that is distal to the tubular centering structure, wherein the distal element comprises a lumen for guide wire insertion.

12. A method for treating restenosis of a lesion region of a patient comprising the steps of:

(g) inserting a balloon catheter through a body conduit to said lesion region of the patient, wherein said balloon catheter comprises a tubular centering structure disposed at a distal section of the balloon catheter, wherein said centering structure comprises a plurality of balloon members that are radially expandable;

(h) inflating each of said plurality of balloon members independently and adjustably in inflation size to stabilize the distal section of the balloon catheter with respect to said lesion region;

(i) inserting a treatment apparatus inside a lumen of the balloon catheter, wherein said treatment apparatus comprises a radiation source;

(j) positioning the radiation source at about the lesion region;

(k) holding the radiation source for a predetermined treatment period for treating restenosis; and (l) withdrawing the treatment apparatus.

13. A method for treating restenosis according to claim 12, wherein said radiation source is selected from the group consisting of beta radiation, gamma radiation, and combination of beta and gamma radiation.

14. A method for treating restenosis according to claim 2, wherein said centering structure is made of material selected from the group consisting of polyurethane, silicone, copolymer of polyurethane and silicone, natural rubber, synthetic rubber, nylon, and latex.

15. A method for treating restenosis according to claim 2, wherein said centering structure is imprinted with radiopaque ink or incorporated with at least one radiopaque marker for tracking exact location of the balloon catheter inside a patient.

* * * * *